United States Patent [19]
Schulte-Elte

[11] 3,968,161
[45] July 6, 1976

[54] PROCESS FOR THE PREPARATION OF DAMASCENONE DERIVATIVES

[75] Inventor: Karl-Heinrich Schulte-Elte, Onex, Geneva, Switzerland

[73] Assignee: Firmenich S.A., Geneva, Switzerland

[22] Filed: July 22, 1975

[21] Appl. No.: 598,132

Related U.S. Application Data

[63] Continuation of Ser. No. 346,296, March 30, 1973, Pat. No. 3,923,896.

[30] Foreign Application Priority Data
Mar. 30, 1972  Switzerland.......................... 4770/72

[52] U.S. Cl. ........................ 260/586 R; 260/563 R; 260/566 R
[51] Int. Cl.² .......................................... C07C 45/00
[58] Field of Search ......... 260/566 A, 586 R, 563 R

[56] References Cited
UNITED STATES PATENTS

| | | | |
|---|---|---|---|
| 3,268,589 | 8/1966 | Rowland .......................... | 260/617 C |
| 3,499,938 | 3/1970 | Hwang et al. .................... | 260/617 C |
| 3,852,355 | 12/1974 | Rautenstrauch ................ | 260/586 R |
| 3,887,625 | 6/1975 | Schulte-Elte .................... | 260/586 R |
| 3,890,370 | 6/1975 | Buchi et al. ..................... | 260/586 R |
| 3,892,809 | 7/1975 | Schulte-Elte .................... | 260/586 R |

OTHER PUBLICATIONS

Salomaa, "Chem. of Carbonyl Group," pp. 202–204 (1966).
Weygand, "Prep. Org. Chem.," pp. 70–74 (1972).

*Primary Examiner*—Norman Morgenstern
*Attorney, Agent, or Firm*—Pennie & Edmonds

[57] ABSTRACT

New alicyclic ketones useful for perfumery and flavor industry and process for preparing same. Use of said compounds as perfuming and/or flavoring, ingredients in the manufacture of perfumes and perfumed products and/or in the preparation of artificial flavors for foodstuffs, beverages, animal feeds, pharmaceutical preparations and tobacco products.

3 Claims, No Drawings

PROCESS FOR THE PREPARATION OF DAMASCENONE DERIVATIVES

This is a continuation, of application Ser. No. 346,296, filed Mar. 30, 1973, now U.S. Pat. No. 3,923,896.

SUMMARY OF THE INVENTION

This invention relates to unsaturated alicyclic ketones having valuable organoleptic properties and useful for perfuming and flavouring a wide range of compositions. The compounds of the present invention may be compounded with other odoriferous compounds, to make perfumery compositions, in a manner conventional in the perfumery art; they may be used, combined with carriers or diluents, for perfuming a wide range of products, and they may also be used to modify the organoleptic properties of foodstuffs, animal feeds, beverages, pharmaceutical preparations and tobacco products.

The compounds to which the present invention relates have the formula:

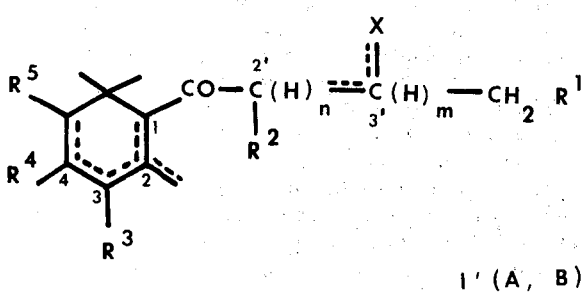

I' (A, B)

wherein:
A: indexes $m$ and $n$ both stand for zero or 1; the ring contains the double bond in position 1, 2 (endocyclic or exocyclic), 3 or 4, or two conjugated double bonds in positions 1 and 3;
the side-chain at position 1 of the ring can contain a double bond in position 2' or 3' as indicated by the dotted lines;
$R^1$ and $R^2$ both represent hydrogen or one of them represents a lower alkyl containing from 1 to 6 carbon atoms and the other hydrogen;
$R^3$, $R^4$ and $R^5$ all represent hydrogen or one of them represents a lower alkyl containing from 1 to 6 carbon atoms and the others hydrogen; and
X represents oxygen (when $m$ = zero and $n$ = 1), or a hydroxyl radical (when $m$ = $n$ = zero);
B:
$m = n = 1$;
the ring contains a double bond in position 1, 2 (endocyclic), 3 or 4, or two conjugated double bonds in positions 1 and 3;
the side-chain at position 1 of the ring contains a single bond in position 2';
$R^1$, $R^2$, $R^3$, $R^4$ and $R^5$ have the same meaning as that indicated above; and
X represents a hydroxyl radical.

With the exception of 2,6,6-trimethyl-1-[1,3-dioxo-but-1-yl]-cyclohex-2-ene, which has been described in Helv. Chim. Acta, 50, 2101 (1967), the compounds of formula I' are new and belong to a class of ketone derivatives which in accordance with the present invention are prepared by:
a. subjecting to a hydrolysis a compound of formula

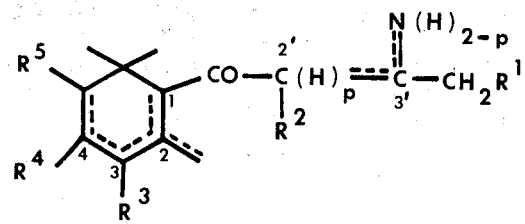

II wherein:
$p$ = zero or 1;
the dotted lines and the symbols $R^1$, $R^2$, $R^3$, $R^4$ and $R^5$ have the meaning aforeindicated, and the side-chain contains a double bond in position 2' (when $p$ = zero) or 3' (when $p$ = 1),
to afford a compound of formula I'A; or
b. subjecting a compound of formula II, as defined above, to a hydrolysis and subsequently reducing the keto-derivative thus obtained to afford a compound of formula I'B.

BACKGROUND OF THE INVENTION

Although the structure of ketones I' is rather similar to that of the ionones or to that of the ketone compounds described in particular in Helv. Chim. Acta, 53, 541, (1970), especially damascenone,

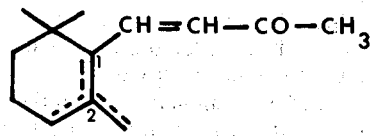

ionones

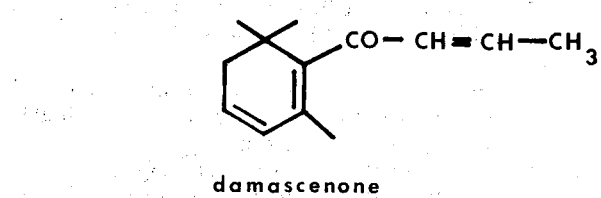

damascenone we have surprisingly found that the odoriferous and flavouring characteristics of the compounds of the present invention are clearly different from those shown by the analogous compounds referred to. This fact illustrates once more the feature of surprise which is generally connected to the phenomena of olfactive and gustative perception. Indeed, we must stress the fact that in spite of the great number of theories hitherto developed in order to define the detection of the specific signaling obtained in the presence of a particular chemical compound, we must admit that at the present state of knowledge there is no theoretical relationship which would enable to predict with certainty the odour or the taste of a given chemical compound.

Whereas the ionones have a typical and intense odour of violets [see for example: P. Z. Bedoukian, Perfumery and Flavouring Synthetics, Elsevier Publ. Co. (1967) and Fortschritte der Chemie organischer Naturstoffe, VIII, 146 (1951)] and the unsaturated ketone compounds of the "damascenone" type [see: Helv. Chim. Acta, 53, 541 (1970)] are odoriferous constituents of distilled Bulgarian rose oil, we have now found that the diketone or keto-hydroxyl compounds of formula I' develop a mint-like, slightly musky odour which is sometimes reminiscent of aromatic herbs such as marjoram.

The novel compounds disclosed in the present application namely include the compounds of formula

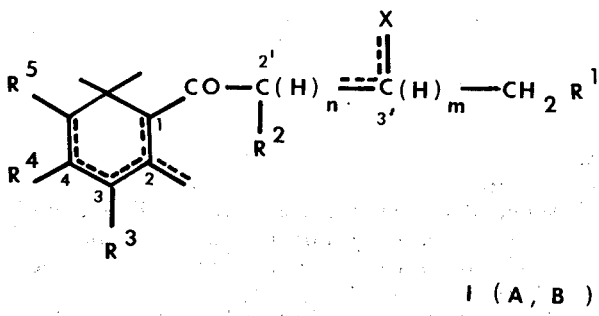

I (A, B)

wherein:
A: indexes $m$ and $n$ both stand for zero or 1;
the ring contains one double bond in position 1, 2 (exocyclic), 3 or 4, or two conjugated double bonds in positions 1 and 3;
the side-chain at position 1 of the ring can contain a double bond in position 2' or 3' as indicated by the dotted lines;
$R^1$ and $R^2$ both represent hydrogen or one of them represents a lower alkyl containing from 1 to 6 carbon atoms and the other hydrogen;
$R^3$, $R^4$ and $R^5$ all represent hydrogen or one of them represents a lower alkyl containing from 1 to 6 carbon atoms and the others hydrogen; and
X represents oxygen (when $m$ = zero and $n$ = 1), or a hydroxyl radical (when $m = N$ = zero);
B: $m = n = 1$;
the ring contains a double bond in position 1, 2 (endocyclic), 3 or 4, or two conjugated double bonds in position 1 and 3;
the side-chain at position 1 of the ring can contain a double bond in position 2' as indicated by the dotted lines;
$R^1$, $R^2$, $R^3$, $R^4$ and $R^5$ have the same meaning as that indicated above;
X represents a hydroxyl radical; and the following derivatives thereof:
2,6,6-Trimethyl-1-[2-methyl-1,3-dihydroxy-but-1-yl]-cyclohex-2-ene,
2,6,6-Trimethyl-1-[2-methyl-1,3-dihydroxy-but-1-yl]-cyclohex-1-ene,
2,6,6-Trimethyl-1-[1,3-dioxo-but-1-yl]-cyclohexane,
2,6,6-Trimethyl-1-[1,3-dihydroxy-but-1-yl]-cyclohexane,
2,6,6-Trimethyl-1-[1,3-dihydroxy-but-1-yl]-cyclohex-2-ene
2,6,6-Trimethyl-1-[1,3-dihydroxy-but-1-yl]-cyclohex-1-ene.

PREFERRED EMBODIMENTS OF THE INVENTION

Depending upon the nature of the products into which compounds I' or the above cited derivatives are incorporated or that of the other constituents present in an odoriferous or flavouring composition and depending on the concentrations at which they are used, they can develop various odoriferous and gustative notes such as animal, fruity, herb-like notes or various combinations of such notes; and they are sometimes reminiscent of the taste and flavour of certain tobaccos. Therefore, compounds of formula I' can be used as perfuming ingredients for the preparation of perfumes and perfumed products.

Particularly, compounds I' and the above cited derivatives are interesting ingredients for the preparation of perfume compositions, e.g. of the "Chypre" type, and for the reconstruction of various artificial essential oils.

The cited compounds also possess very interesting flavouring properties and consequently, can be used as flavouring agents or as additives destined to modify the organoleptic properties of foodstuffs, animals feeds, beverages, pharmaceutical preparations and tobacco. They can develop floral, camphor-like, woody notes and they are sometimes reminiscent of the odour and taste of certain berries, e.g. bilberries.

The term "foodstuff" is used broadly herein; the compounds of the invention may be incorporated into products such as tea, coffee and cocoa.

The proportions of the said compounds to be used in order to achieve an interesting odoriferous or gustative effect vary within a wide range. For example in the preparation or perfume compositions, interesting effects can be obtained when the compounds of the invention constitute as little as 500 ppm. of the total weight of the perfumed composition, or as much as 5 or even 10% of the total composition, particularly when special odoriferous effects are sought.

Similarly, the proportions used for flavouring purposes can also vary widely. Typically, interesting flavouring effects can be achieved with amounts ranging from about 0.1 to about 10 ppm., based on the total weight of the product flavoured. However, these proportions can be raised beyond the indicated limits; in admixture with other flavouring agents, they may typically be comprised from 0.5 to 15% of the total weight of the composition.

According to a preferred mode of execution of the process of the present invention the hydrolysis of compounds II is carried out by means of an acidic agent, e.g. a strong mineral acid. A hydrogen halide, e.g. hydrochloric or hydrobromic acid, or sulphuric or phosphoric acid can be used. Suitable acidic reagents include organic acids, e.g. p-toluenesulphonic or formic acid; hydrochloric acid is however preferred. The hydrolysis is preferably performed in an aqueous medium in the presence of an inert organic solvent. Suitable solvents include common organic solvents such as alcohols, e.g. methanol, ethanol or isopropanol, or ethers such as dioxan, tetrahydrofuran or monoglyme, or a mixture of at least two of the said solvents. Aqueous methanol is preferred.

The said hydrolysis may occur in a wide temperature range. The formation of compounds I' was observed at temperatures from about 15° to about 100°C, however, it has been observed that the best yields of final product are obtained when the hydrolysis is performed at a temperature in the vicinity of the boiling temperature of the selected solvent.

The process of the invention is illustrated by the following reaction scheme:

aluminium hydride or sodium and boron hydride. However, when using the said metal reagents, it is sometimes difficult to interrupt the reaction at the first stage as the reduction takes place also on the second keto-

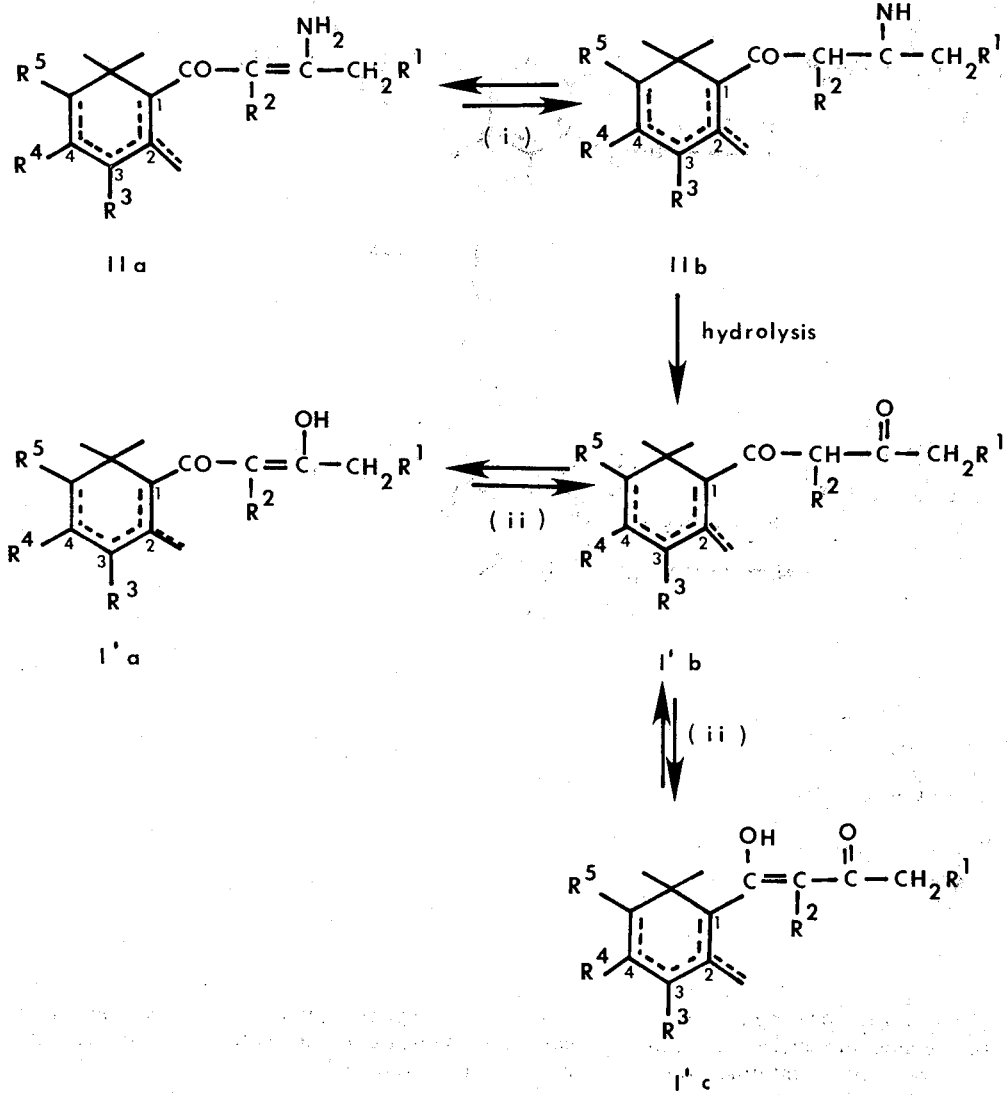

(i) and (ii) represent imino-amino and keto-enol equilibrium reactions, respectively.

By reduction of the obtained compounds I'a, I'b or I'c, in particular those which contain a single double bond in position 1 or 2 of the ring, compounds of formula

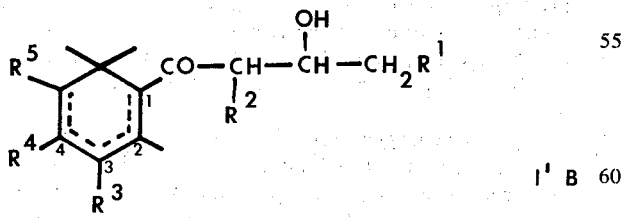

are obtained.

The said reduction is preferably carried out by catalytic hydrogenation in the presence of Raney nickel, palladium or platinum oxide. It can also be effected by means of the conventional metal reagents commonly used to promote the conversion of a keto-group into a secondary alcohol group, e.g. by means of lithium and group present in the molecule whereby dihydroxyl compounds having the formula

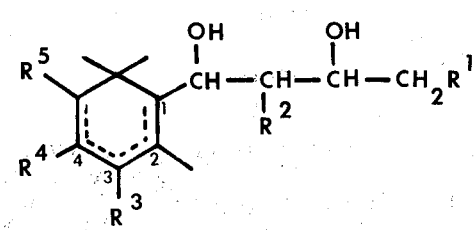

are obtained.

It has been observed that the best yields of hydroxyketone I'B are reached when the reduction is carried out in a neutral or slightly alkaline medium.

The compounds of formula II, used as starting materials in the process of the invention, can be prepared according to the synthetic method described in our copending application Ser. No. 343,490, filed Mar. 21, 1973, now U.S. Pat. No. 3,931,323. The said method can be illustrated by the following reaction scheme:

SCHEME A:

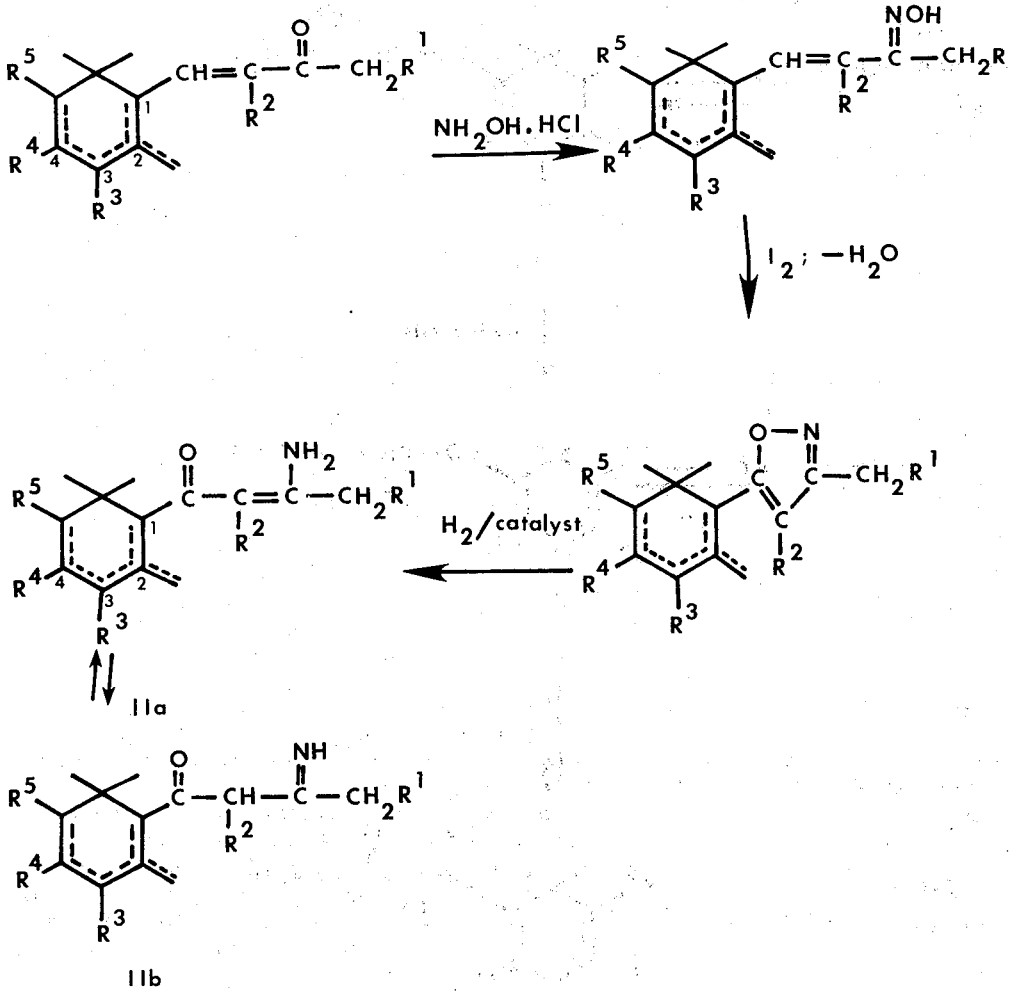

Apart from being useful in their own right by virtue of their valuable organoleptic properties, the compounds of formula I' are also useful as intermediates in the preparation of compounds of formula

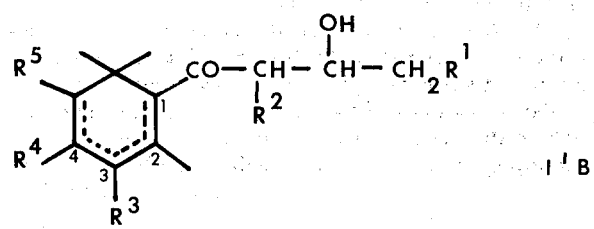

wherein $R^1$, $R^2$, $R^3$, $R^4$ and $R^5$ as well as the dotted lines have the meaning already given, which are also useful as odoriferous or flavouring agents [cf. French patent No. 1,591,031; Swiss patents Nos. 513,094; 513,096; 513,097; Helv. Chim. Acta, 53, 541 (1970)]. For instance compounds III can be obtained by dehydrating a compound having the formula The said dehydration is preferably effected by means of an acidic or basic agent or by the action of heat. Suitable dehydration reagents include mineral acids, such as sulphuric, hydrochloric, boric or phosphoric acid, or an organic acid, such as p-toluenesulphonic acid. Oxides, e.g. phosphoric acid anhydride, or organic acid anhydrides, e.g. acetic anhydride, can also promote the said dehydration.

Strong bases can also be used. In this case, however, there were obtained secondary products, probably formed by reactions other than the mere dehydration.

The above described conversion of compounds I' into compounds III represents a technically original solution of the problem brought up by the synthesis of unsaturated alicyclic ketones III. Most of these compounds and various processes for their preparation have been described in the past. The synthetic methods used heretofore for the preparation of such compounds include:

a. partial hydrogenation of the corresponding acetylenic derivatives [Swiss Patent No. 498,795];

b. direct condensation of an organo-metallic propene derivative with a cyclogeranoyl derivative [Swiss Patent No. 503,684];

c. cyclization of a "pseudo-ketone" by means of an acidic cyclization agent [Swiss Patent No. 503,685];

d. dehydrogenation of a cyclohexenic ketone to obtain the corresponding cyclohexadienic derivative [Swiss Patent No. 505,773].

The above indicated conversion has the advantages of affording better yields and using more readily accessible starting materials than the earlier processes.

The compounds of formula I' comprising an exocyclic double bond in the ring can be converted into their corresponding saturated derivatives by means of the reduction techniques conventional in the art. The hereinbelow scheme will illustrate various reactions to which compounds I' and some of their derivatives may undergo.

SCHEME B

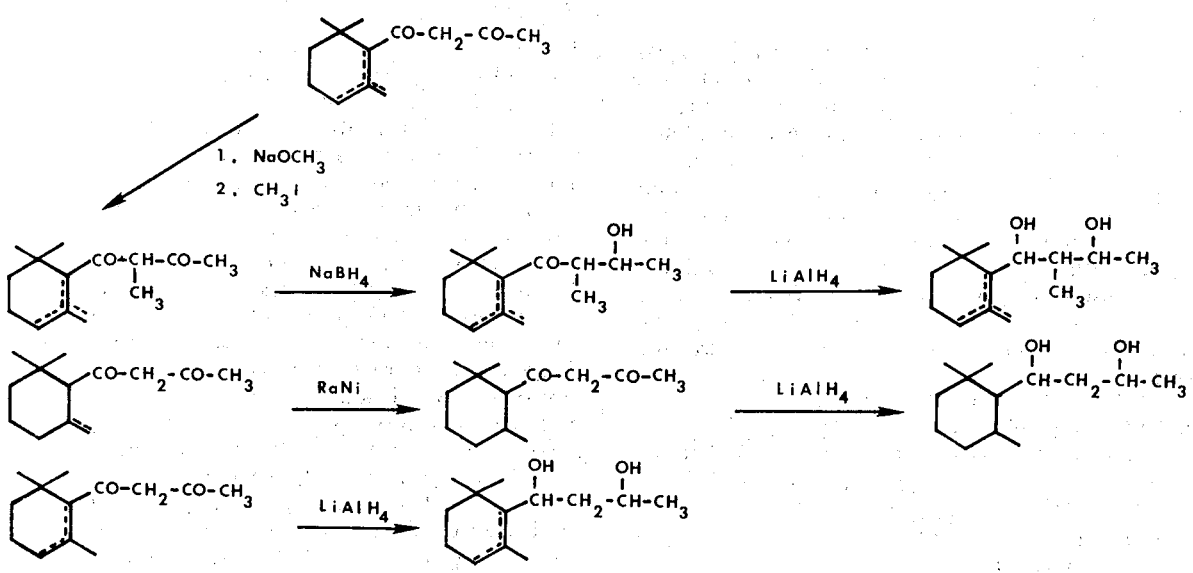

The above scheme is intended to serve as an example.

The invention is illustrated by the following examples, in which all the temperatures are indicated in degrees centigrade and the abbreviations have the meaning conventional in the art.

EXAMPLE 1

2,6,6-Trimethyl-1-[1,3-dioxo-but-1-yl]-cyclohex-2-ene 23 g of 2,6,6-trimethyl-1-[3-amino-but-2-en-1-oyl]-cyclohex-2-ene in 150 ml of methanol were kept at reflux for 4 hours in the presence of 110 ml of a 10 % aqueous solution of hydrochloric acid in water. After cooling the reaction mixture was extracted with ether (4 fractions of 100 ml each), and the combined organic extracts were washed with a sodium bicarbonate solution until neutrality. After concentration under reduced pressure, the fractional distillation of the residue provided 21 g (yield 92 %) of the desired diketone; b.p. 62°–65°/0.01 Torr.

$n_D = 1.5079$; $d^{20} = 0.9883$

IR : 2900, 1610 cm$^{-1}$

NMR : 0.9 and 0.94 (6H, 2s); 1.6 (3H, broad band, s); 2.02 (3H, s); 5.4 (1H, s); 5.52 (1H, m) δ ppm MS : M$^+$ = 208 (6); m/e: 175 (0.1); 150 (3); 135 (1); 124 (8); 109 (18); 85 (100); 69 (3); 55 (3); 43 (25); 27 (18).

The 2,6,6-trimethyl-1-[3-amino-but-2-en-1-oyl]-cyclohex-2-ene, used as starting material in the above indicated preparation, can be prepared as follows.

77 g of hydroxylamine hydrochloride and 125 g of anhydrous sodium acetate in 200 ml of water were added to a solution of 200 g of α-ionone in 500 ml of ethanol. The reaction was slightly exothermic and the temperature rose to about 35°. After stirring of the reaction mixture for 15 minutes, the volatile portions were distilled off under reduced pressure. The residual aqueous solution was then diluted with 200 ml of water and extracted with two fractions of 150 ml each of petroleum-ether (b.p. 80°–100°). The combined organic extracts were washed with water and a 10 % diluted solution of sodium hydrogenocarbonate until neutrality. The evaporation of the volatile portions resulted in a residue constituted by α-ionone oxime (210 g). An analytical sample was prepared by purification by means of thin layer chromatography.

b. A solution of 88.9 g of sodium hydrogenocarbonate in 750 ml of water was added, while stirring to a solution of 53.0 g of α-ionone oxime (0.260 mole) in 750 ml of tetrahydrofuran.

The process was then carried on in the absence of light, and a solution of 148.6 g of potassium iodide and 69.2 g of iodine (0.270 mole) in 500 ml of water was added. After refluxing for 7 hours, the solution was allowed to stand overnight. After dilution with 500 ml of a concentrated solution of sodium bisulphite in water, the reaction mixture was extracted with ether (750 ml) and the combined organic extracts were dried over anhydrous sodium sulphate and concentrated under reduced pressure. Distillation of the thus obtained residue yielded 28.75 g of 3-methyl-3-[2,6,6-trimethyl-cyclohex-2-en-1-yl]-isoxazole with a yield of 54 %. B.p. 69°–70°/0.04 Torr.

IR (CHCl$_3$) : 2960, 1595, 1445, 1415 cm$^{-1}$

NMR (CDCl$_3$) : 0.73 (3H, s); 0.99 (3H, s); 1.55 (3H, m); 2.22 (3H, s); 2.92 (1H, broad band, S); 5.49 (1H, m); 5.68 (1H, s); 1.2 – 2.2 (4H, multiplet) δ ppm UV (95 % ethanol) : nm max 218 (ε 9750).

MS (70 eV) : M$^+$ = 205.

4.10 g (0.020 mole) of 3-methyl-5-[2,6,6-trimethyl-cyclohex-2-en-1-yl]-isoxazole were dissolved in 5 ml of anhydrous ethanol and the solution was added to 0.173 g of a mixture of 83.6 % of platinum oxide in 30 ml of ethanol, the said mixture having previously been subjected to a hydrogenation. The solution was then subjected to a hydrogenation at room temperature and at atmospheric pressure and, after absorption of one equivalent of hydrogen, filtered through a "Celite" carrier. After having been concentrated under reduced pressure the residual solution was subjected to chromatography on a magnesium silicate column by elution with a mixture of chloroform/hexane (25/75) to yield 3.73 g (yield: 90 %) of 2,6,6-trimethyl-1-[3-amino-but-2-en-1-oyl]-cyclohex-2-ene.

IR (CHCl$_3$) : 3485, 2950, 1615, 1590, 1520 cm$^{-1}$
NMR (CDCl$_3$) : 0.89 (6H, s); 1.58 (3H, m); 1.90 (3H, s); 2.38 (1H, broad band, s); 5.06 (1H, broad band, s); 5.50 (1H, m); 1.2 – 2.3 (4H, multiplets) δ ppm
UV (95 % ethanol) : nm max 301 (ε 18,400)
MS (70 eV) : M$^+$ = 207.

2,6,6-Trimethyl-1-[3-hydroxy-butan-1-oyl]-cyclohex-2-ene a. by catalytic hydrogenation:
4.16 g (0.02 mole) of the diketone prepared as described above in 50 ml of methanol were subjected to a hydrogenation in the presence of about 0.5 g of Raney nickel and of a small amount of KOH. After absorption of about 450 ml of hydrogen - the said absorption proceeding within about 20 hours - the reaction mixture was filtered, the volatile portions were evaporated and the residue was first taken up in petroleum-ether, then washed with water and sodium bicarbonate until neutrality. Distillation gave 3.6 g of an oil which, by separation by means of vapour phase chromatography, yielded 3.1 g (yield 74 %) of the desired hydroxyketone.

$n_D$ = 1.4841; d$^{20}$ = 0.9870
IR : 3450 and 1705 cm$^{-1}$
NMR : 0.9 (6H, s); 1.09 (3H, d,J=7cps); 1.6 (3H, m); 2.6 (1H, s); 4.0 (1H, m); 5.5 (1H, m) δ ppm
MS : M$^+$ = 210 (5); m/e: 192 (2); 166 (3); 151 (0.5); 135 (0.5); 123 (85); 109 (8); 87 (60); 69 (61); 55 (5); 43 (100); 29 (5).

By separation by means of vapour phase chromatography there was also obtained 0.5 g of 2,6,6-trimethyl-1-[1,3-dihydroxybut-1-yl]-cyclohex-2-ene.
MS : 109 (16); 91 (5); 85 (32); 69 (5); 43 (40); 27 (4).

b. by reduction by means of LiAlH$_4$:
1.6 g of the diketone prepared as described above in 50 ml of ether were treated, while stirring and cooling, with 0.4 g of lithium-aluminium hydride in 30 ml of ether. 5 minutes are needed to complete the addition of LiAlH$_4$. Then methanol and water were added to the reaction mixture which was afterwards extracted with ether. After separation, the combined organic extracts were washed with water, neutralized with a 10 % solution bicarbonate and finally the volatile portions were evaporated. The resulting residue was distilled to give 1.5 g of a mixture containing 35 % of the desired hydroxyketone.

2,6,6-Trimethyl-1-[3-hydroxy-butan-1-oyl]-cyclohex-2-ene can be converted into 2,6,6-trimethyl-[but-2-en-1-oyl]-cyclohex-2-ene as follows:

1.0 g of 2,6,6-trimethyl-1-[3-hydroxy-butan-1-oyl]-cyclohex-2-ene, in about 25 ml of methylene chloride, was heated for 60 minutes at about 40° in the presence of a small amount of p-toluenesulphonic acid. After extraction with ether the combined organic extracts were washed with a 10 % sodium bicarbonate solution and then with water. After drying over anhydrous MgSO$_4$, the evaporation of the ether gave a residue which, after distillation, yielded the desired ketone, (yield 90 %). The analytical data were identical with those of a pure sample prepared according to one of the known methods [cf. Swiss patent No. 503,685].

EXAMPLE 2

2,6,6-Trimethyl-[1,3-dioxo-but-1-yl]-cyclohex-1-ene 30 g of 2,6,6-trimethyl-1-[3-amino-but-2-en-1-oyl]-cyclohex-1-ene in 150 ml methanol were reacted at room temperature with 130 ml of a 10 % solution of phosphoric acid. The complete conversion of the starting material took place within 12 hours. After cooling the mixture was taken up with petroleum-ether and the organic petroleum-ether extracts were washed with water until neutrality. After concentration under reduced pressure, the residue obtained gave by fractional distillation 28.5 g (yield 95 %) of the desired diketone-B.p. 75°–7°/0.15 Torr; $n_D$ = 1.5141, d$^{20}$ = 1.004
IR : 2600, 1610 cm$^{-1}$;
NMR : 1.05 (6H, 2s); 1.65 (3H, s); 2.05 (3H, s); 5.3 (1H, s) δ ppm
MS : M$^+$ = 208 (12); m/e: 193 (100), 175 (5); 165 (7); 150 (10); 135 (16); 123 (16); 109 (16); 91 (5); 85 (32); 69 (5); 55 (5); 43 (40); 27 (4).

The 2,6,6-trimethyl-1-[3-amino-but-2-en-1-oyl]-cyclohex-1-ene used as starting material in the above indicated preparation can be prepared as follows. a. 77 g of hydroxylamine hydrochloride and 125 g of anhydrous sodium acetate in 200 ml of water were added to a solution of 200 g of β-ionone in 500 ml of ethanol. The rection was slightly exothermic and the temperature rose to about 35°. The reaction mixture was stirred for 15 more minutes and the volatile portions were distilled off under reduced pressure. The residual aqueous solution was then diluted with 200 ml of water and extracted with two fractions of 150 ml each of petroleum-ether (b.p 80°–100°). The combined organic extracts were washed with water and a 10% diluted solution of sodium hydrogenocarbonate until neutrality. The evaporation of the volatile portions resulted in a residue constituted by the desired β-ionone oxime (210 g). An analytical sample was prepared by purification by means of thin layer chromatography. The obtained product had a b.p. of 90°/0.001 Torr.

b. A solution of sodium hydrogenocarbonate (136 g) in 1300 ml of water was added, while stirring, to a solution of β-ionone oxime (85 g; 0.410 mole) in 1500 ml of tetrahydrofuran.

The process was then carried on in the absence of light, and a solution of potassium iodide (235 g; 1.41 moles) and iodine (109 g; 0.43 mole) in 1000 ml of water was added. After having been refluxed for 4 hours, the solution was allowed to stand overnight. After dilution with 1500 ml of a concentrated solution of sodium bisulphite in water the reaction mixture was extracted with ether (3 litres) and the combined organic extracts were dried over anhydrous sodium sulphate and concentrated under reduced pressure. The fractional distillation of the thus obtained residue yielded 77.2 g of 3-methyl-5-[2,6,6-trimethyl-cyclohex-1-en-1-yl]-isoxazole (yield 91 %), b.p. 70°–71°/0.03 Torr.
IR (CHCl$_3$): 2930, 1655, 1585, 1410 cm$^{-1}$
NMR (CDCl$_3$): 1.00 (6H, s); 1.50 (3H, s); 2.27 (3H, s); 5.86 (1H, s); 1.5 – 2.2 (6H, multiplets) δ ppm
UV (95 % ethanol): nm max 209, 224
MS (70 eV): M$^+$ = 205.

c. 30.75 g (0.15 mole) of 3-methyl-5-[2,6,6-trimethylcyclohex-1-en-1-yl]-isoxazole were dissolved in 50 ml of dry ethanol and the solution was added to 1.396 g of a mixture of 82.9 % of platinum oxide in 600 ml of ethanol, the said mixture having previously been subjected to a hydrogenation. The alcoholic solution was then subjected to a hydrogenation at ordinary temperature and pressure and, after absorption of one equivalent of hydrogen, was filtered through a Celite carrier. After having been concentrated under reduced pressure, the residual mixture was recrystallized from hexene containing traces of ethanol to yield 30.91 g (yield 100 %) of 2,6,6-trimethyl-1-[3-amino-but-2-enoyl]-cyclohex-1-ene which exists in two interconvertible crystalline structures: m.p. 124.5° – 125.0° and 135°–136°.
IR (CHCl₃): 3490, 1610, 1510 cm⁻¹
NMR (CDCl₃): 1.09 (6H, s); 1.56 (3H, s); 1.92 (3H, s); 5.00 (1H, broad band, s); 1.4 – 2.1 (6H, multiplets) δ ppm
UV (95 % ethanol): nm max 303 (ε 20,100)
MS (70 eV): M⁺ = 207.

2,6,6-Trimethyl-1-[3-hydroxy-butan-1-oyl]-cyclohex-1-ene a. by catalytic hydrogenation:

4.2 g of diketone prepared as described above in 75 ml of ethanol were subjected to a hydrogenation according to the procedure described in Example 1. There were thus obtained 4.0 g of the desired hydroxyketone (yield 95 %); b.p. about 75°/0.01 Torr; $n_D$ = 1.4883; $d^{20}$ = 0.9968
IR: 3450, 1690 cm⁻¹
NMR: 1.07 (6H, s); 1.10 (3H, d, J=7 cps); 1.56 (3H, s); 4.1 (1H, m) δ ppm
MS: M⁺ = 210 (5); m/e: 192 (18); 177 (36); 166 (8); 171 (100); 135 (15); 123 (98); 109 (18); 91 (10); 81 (48); 69 (26); 55 (12); 43 (63); 29 (14).

b. by reduction by means of LiAlH₄:

By proceeding as indicated in Example 1 and starting from the diketone prepared as described in that same Example there will be obtained 2,6,6-trimethyl-1-[3-hydroxy-butan-1-oyl]-cyclohex-1-ene in a yield of 30-40 %.

2,6,6-Trimethyl-1-[3-hydroxy-butan-1-oyl]-cyclohex-1-ene can be converted into 2,6,6-trimethyl-[but-2-en-1-oyl]-cyclohex-1-ene according to the procedure given in Example 1 for the conversion of the corresponding cyclohex-2-ene derivative. In this case, however, toluene was used as the solvent, and the cyclization was carried out at about 100°–110°.

The analytical data were identical with those of a pure sample prepared according to one of the known methods [cf. Swiss patent No. 505,773].

In accordance with the procedure described in Examples 1 and 2, the following compounds were prepared.

2,6,6-Trimethyl-1-[2-methyl-1,3-dioxo-1-but-1-yl]-cyclohex-1-ene $n_D$ = 1.4979; $d^{20}$ = 0.9942
IR: 1700 and 1600 cm⁻¹
NMR: 0.86 and 0.94 (6H, s); 1.28 (3H, d, J=8 cps); 1.59 (3H, s); 5.48 (1H, m) δ ppm
MS: M⁺ = 222 (5); m/e; 207 (0.1); 165 (0.5); 150 (36); 135 (5); 123 (72); 107 (18); 99 (100); 81 (33); 67 (10); 57 (14); 43 (76); 27 (7).

2,6,6-Trimethyl-1-[2-methyl-1,3-dioxo-1-but-1-yl]-cyclohex-2-ene $n_D$ = 1.5129; $d^{20}$ = 0.9926
IR: 2800 and 1580 cm⁻¹
NMR: 0.95 and 1.14 (6H, 2s); 1.56 (3H, s); 1.71 (3H, s); 2.12 (3H, s) δ ppm
MS: M⁺ = 222 (5); m/e: 207 (100); 191 (1); 179 (1); 165 (10); 151 (20); 139 (13); 123 (16); 109 (8); 99 (16); 81 (12); 67 (5); 55 (10); 43 (40); 27 (6).

2-Methylene-6,6-dimethyl-1-[2-methyl-1,3-dioxo-1-but-1-yl]-cyclohexane $n_D$ = 1.4897; $d^{20}$ = 0.9815
IR: 3080, 1725, 1690, 1640 and 900 cm⁻¹
NMR: 0.9 (6H, s); 1.2 (3H, d, J=7 cps); 2.05 (3H, s); 4.7 and 4.86 (2H, 2m) δ ppm
MS: M⁺ = 222 (1); m/e: 207 (2); 193 (1); 179 (6); 150 (60); 135 (32); 123 (52); 107 (17); 99 (40); 81 (38); 69 (16); 55 (16); 43 (100); 27 (9).

2-Methylene-6,6-dimethyl-1-[1,3-dioxo-1-but-1-yl]-cyclohexane $n_D$ = 1.5058; $d^{20}$ = 0.9790
IR: 3080, 2600, 1640, 1610, 890 cm⁻¹
NMR: 0.9 and 0.98 (6H, 2s); 1.96 (3H,s); 4.65 and 4.77 (2H, 2m); 5.34 (3H, s) δ ppm The starting materials for the above preparations were prepared as follows:

for
2,6,6-Trimethyl-1-[2-methyl-1,3-dioxo-1-butyl]-cyclohex-1-ene:

a. 16 g of hydroxylamine hydrochloride in 60 ml of water were added to a solution of α-isomethyl ionone (41.2 g; 0.200 mole) in ethanol, kept under vigorous stirring. 22 g of sodium hydrogenocarbonate were then added to the said solution in small portions and the thus obtained mixture was refluxed for 24 hours. After cooling, the said mixture was poured into 250 ml of water, extracted with ether (750 ml) and with methylene chloride (130 ml). The combined organic extracts were dried over magnesium sulphate and concentrated under reduced pressure to give 43.6 g of the desired oxime. There were obtained 41.1 g of α-isomethyl ionone oxime (yield 93 %): b.p. 110°–112°/0.05 Torr, by fractional distillation.
IR (CHCl₃): 3560, 3250, 2900, 1630 cm⁻¹
NMR (CDCl₃): 0.79 (3H, s); 0.92 (3H, s); 1.53 (3H, m); 1.94 (3H, broad band, s); 2.06 (3H, s); 2.66 (1H, d, J=10 cps); 5.41 (1H, m); 5.69 (1H, d of q, J=10, 0.5 cps); 9.85 (1H, broad band); 1.2 – 2.2 (4H, multiplets) δ ppm
UV (95 % ethanol): nm max 236 (ε 22,800)
MS (70 eV): M⁺ = 221.

b. A solution of sodium hydrogenocarbonate (4.50 g) in 25 ml of water was added, while stirring, to a solution of α-isomethyl ionone oxime (2.42 g; 0.011 mole) in 30 ml of tetrahydrofuran.

The process was then carried on in the absence of light, and a solution of potassium iodide (5.80 g) and iodine (2.84 g; 0.011 mole) in 15 ml of water was added. After having been refluxed for 18 hours, the reaction mixture was poured into a concentrated solution of sodium bisulphite (130 ml), extracted with ether (150 ml), and the organic extracts were dried over sodium sulphate and concentrated under reduced pressure. The fractional distillation of the obtained residue yielded 1.380 g of 3,4-dimethyl-5-[2,6,6-trimethyl-cyclohex-2-en-1-yl]-isoxazole (yield 57 %): b.p. 72°–74°/0.04 Torr.
IR (CHCl₃): 2910, 1620, 1440, 1414 cm⁻¹
NMR (CDCl₃): 0.72 (3H, s); 1.00 (3H, s); 1.50 (3H, m); 1.90 (3H, s); 2.14 (3H, s); 2.96 (1H, broad band, s); 5.63 (1H, m); 1.2 – 2.2 (4H, multiplets) δ ppm
UV (95% ethanol): nm max 225 (ε 8150)
MS (70 eV): M⁺ = 219.

c. By a treatment of the thus obtained isoxazole according to the procedure described in Example 1, paragraph c, there was obtained 2,6,6-trimethyl-1-[3-amino-2-methylbut-2-en-1-oyl]-cyclohex-2-ene.

for
2-methylene-6,6-dimethyl-1-[1,3-dioxo-1-butyl]-cyclohexane:

a. A solution of 30 g of γ-ionone in 75 ml of ethanol was added to a solution of hydroxylamine hydrochloride (12 g) and sodium acetate (21.6 g) in 30 ml of water. The addition was completed within 5 minutes. The reaction was slightly exothermic, the reaction mixture was stirred for 30 minutes, then it was concentrated under reduced pressure. Thereafter 30 ml of water and 30 ml of ether were added to the said mixture, and it was extracted with petroleum-ether. After drying and concentration, the combined organic extracts yielded a thick oil (31.2 g). An aliquot was distilled in a small distillation tube at a temperature of 180° and a pressure of 0.001 Torr. There was thus obtained a pure product which, as shown by vapour phase chromatography, constituted a mixture of the γ-ionone oxime in the form of the two syn- and anti-isomers in a ratio of 20:80.

$n_D = 1.5294$; $d_4^{20} = 0.970$.
IR: 3250, 1640, 980, 888 cm$^{-1}$
NMR: 0.85 and 0.92 (6H, 2s); 2.01 (3H, s); 4.54 and 4.72 (2H, 2m); 6.1 (2H, d, J=5 cps) δ ppm
MS: M$^+$ = 207 (0.1); m/e: 191 (1); 176 (3); 159 (2); 148 (1); 136 (3); 123 (4); 107 (3); 91 (2); 81 (3); 69 (3); 58 (20); 43 (100); 27 (38).

b. A solution of sodium hydrogenocarbonate (13.6 g) in 230 ml of water was added to a solution of γ-ionone oxime (8.5 g) in 150 ml of tetrahydrofuran.

The process was then carried on as indicated in Example 1 by adding to the above mentioned solution a solution of potassium iodide (23.5 g) and iodine (10.9 g), whereupon the solution was refluxed for 4 hours. After cooling the solution was extracted with petroleum-ether. After the usual treatment of drying and evaporation of the volatile portions the combined organic extracts yielded 8.4 g of crude product which, by fractional distillation, gave 6.0 g of the desired isoxazole in the form of a yellowish oil. B.p. 130°/0.001 Torr. The analysis carried out by means of a sample obtained by vapour phase chromatography ("Carbowax" column, 3 m, 180°) showed that the obtained product was constituted by two substances in a ratio by weight of 80:20, the main product being 3-methyl-5-[2-methylene-6,6-dimethyl-cyclohexyl]-isoxazole.

$n_D = 1.5025$; $d_4^{20} = 1.005$.
IR: 3080, 1640, 1590, 890 cm$^{-1}$
NMR: 0.92 (6H, 2s); 2.21 (3H, s); 3.3 (1H, s); 4.58 and 4.76 (2H, 2m); 5.75 (1H, s) δ ppm
MS: M$^+$ = 205 (23); m/e: 190 (13); 177 (25); 162 (8); 149 (10); 137 (100); 122 (10); 108 (15); 97 (13); 82 (15); 69 (63); 55 (13); 41 (50); 27 (38).

c. 4.1 g of 3-methyl-5-[2-methylene-6,6-dimethyl-cyclohexyl]-isoxazole in 10 ml of anhydrous ethanol were subjected to a hydrogenation in the presence of a small amount of Raney nickel and of KOH. After absorption of 440 ml of hydrogen (corresponding to about 90% of the theoretical amount) the solution was filtered, washed until neutrality and concentrated to yield an oily residue (4 g). By separation by means of vapour phase chromatography (Carbowax column, 1.5 m) there was obtained in a yield of 80% 2-methylene-6,6-dimethyl-1-[3-amino-but-2-enoyl]-cyclohexane.

$n_D = 1.5448$; $d^{20} = 1.009$.
IR: 3400, 1620, 888 cm$^{-1}$

MS: M$^+$ = 207 (3); m/e: 163 (1); 150 (1); 136 (2); 123 (2); 109 (3); 93 (3); 84 (100); 69 (8); 55 (3); 41 (9); 29 (2).

2,6,6-Trimethyl-1-[2-methyl-1,3-dioxo-1-butyl]-cyclohex-1-ene can be snythetized by methylation of the corresponding 2,6,6-trimethyl-1-[1,3-dioxo-1-butyl]-cyclohex-1-ene according to the alkylation techniques conventional in the art (e.g.: by means of CH$_3$I in the presence of NaOCH$_3$).

Similarly, 2-methylene-6,6-dimethyl-1-[2-methyl-1,3-dioxo-1-butyl]-cyclohexane can be obtained from the corresponding 2-methylene-6,6-dimethyl-1-[1,3-dioxo-1-butyl]-cyclohexane.

According to the conventional techniques (see above-given scheme B) the following compounds were prepared.

2,6,6-Trimethyl-1-[2-methyl-3-hydroxy-butan-1-oyl]-cyclohex-2-ene $n_D = 1.4895$; $d^{20} = 1.005$;
IR: 3450, 1705, 815 cm$^{-1}$;
NMR: 0.91 and 1.1 (6H, 2 s); 1.6 (3H, s); 4.0 (1H, m); 5.5 (1H, m) δ ppm
MS: M$^+$ = 224 (0); m/e: 206 (0.1); 180 (22); 165 (1); 151 (1); 137 (1); 123 (100); 101 (8); 91 (14); 81 (54); 67 (12); 57 (89); 41 (20); 29 (33).

2,6,6-Trimethyl-1-[2-methyl-1,3-dihydroxy-but-1-yl]-cyclohex-2-ene $n_D = 1.4949$; $d^{20} = 0.9974$
IR: 3400 cm$^{-1}$;
NMR: 0.87 and 0.93 (6H, 2s); 1.8 (3H, s); 4.0 (1H, m); 5.5 (1H, m) δ ppm
MS: M$^+$ = 226 (0); m/e: 180 (0.1); 159 (5); 124 (33); 109 (100); 93 (10); 81 (22); 67 (19); 57 (30); 43 (55); 29 (22).

2,6,6-Trimethyl-1-[2-methyl-1,3-dihydroxy-but-1-yl]-cyclohex-1-ene m.p. 107°–109°;
NMR: 0.98 and 1.13 (6H, 2s); 1.25 (3H, d, J=7 cps); 1.86 (3H, s); 4.15 (1H, m); 4.6–4.75 (1H, 2d, J=3 cps) δ ppm
MS: M$^+$ = 226 (0.1); m/e: 212 (1); 184 (13); 179 (18); 161 (20); 153 (95); 135 (100); 123 (46); 109 (68); 93 (65); 81 (44); 69 (62); 55 (60); 43 (80); 29 (40).

2-Methylene-6,6-dimethyl-1-[2-methyl-3-hydroxy-butan-1-oyl]cyclohexane $n_D = 1.4939$; $D^{20} = 0.9974$;
IR: 3450, 3080, 1700, 1640, 885 cm$^{-1}$
NMR: 0.9 and 0.96 (6H, 2s); 3.8 (1H, m); 4.78 and 4.88 (2H, 2m) δ ppm
MS: M$^+$ = 224 (0.1); m/e: 303 (0.1); 180 (10); 165 (4); 151 (4); 137 (3); 123 (40); 109 (20); 101 (9); 81 (30); 69 (12); 57 (100); 41 (30); 29 (38).

2,6,6-Trimethyl-1-[1,3-dioxo-but-1-yl]-cyclohexane $n_D = 1.4891$; $d^{20} = 0.9736$;
IR: 1720, 1690, 1600 cm$^{-1}$
NMR: 0.75–1.3 and 1.8–2.1 δ ppm;
MS: M$^+$ = 224 (2); m/e: 209 (1); 192 (1); 181 (1); 163 (4); 152 (20); 141 (6); 125 (60); 109 (12); 99 (40); 83 (36); 69 (100); 55 (30); 43 (55); 29 (20).

2,6,6-Trimethyl-1-[1,3-dihydroxy-but-1-yl]-cyclohexane $n_D^{20} = 1.4906$; $d^{20} = 0.9845$;

IR: 3400 cm$^{-1}$;
NMR: 0.85–1.3 and 4.1 δ ppm;
MS: M$^+$ = 214 (0); m/e: 196 (0.1); 163 (5); 153 (11); 135 (11); 135 (7); 123 (22); 111 (35); 89 (97); 83 (97); 83 (33); 69 (100); 55 (47); 45 (82); 29 (16).

2,6,6-Trimethyl-1-[1,3-dihydroxy-but-1-(-yl])-cyclohex-2-ene n$_D$ = 1.4933; d$^{20}$ = 0.9936;
IR: 3400, 815 cm$^{-1}$;
NMR: 0.85 and 0.99 (6H, 2s); 1.1 (3H, d, J=7 cps); 1.75 (3H, s); 5.35 (1H, m) δ ppm;
MS: M$^+$ = 212 (0); m/e: 205 (5); 194 (6); 176 (3); 161 (4); 149 (24); 138 (6); 123 (70); 109 (100); 94 (50); 81 (67); 71 (50); 55 (48); 43 (98); 29 (34).

2,6,6-Trimethyl-1-[1,3-dihydroxy-but-1-yl]-cyclohex-1-ene m.p. 124-5°
IR: 3400 cm$^{-1}$;
NMR: 1.5 (3H, d, J=8 cps); 1.85 (3H, s); 4.1 (1H, m); 4.55 (3H, m) δ ppm
MS: M$^+$ = 212 (3); m/e: 194 (17); 179 (18); 153 (80); 135 (100); 121 (47); 109 (55); 93 (60); 79 (44); 69 (55); 55 (44); 43 (82); 29 (33).

Example 3

Perfume composition of the Chypre type

A perfume composition of the Chypre type was obtained by mixing the following ingredients (parts by weight);

| | |
|---|---|
| Bergamot | 21 |
| Sweet orange oil | 0.5 |
| Synthetic neroli | 1 |
| Synthetic rose | 9 |
| Synthetic jasmin | 9 |
| Ylang extra | 6 |
| Methylionone | 6 |
| Hydroxycitronellal | 6 |
| Santal oriental | 3 |
| Patchouli | 1.5 |
| Vetyveryl acetate | 4.5 |
| Natural degreased civet, 10 %* | 3 |
| Labdanum ciste absolute, 10 %* | 2 |
| Musk ketone | 4 |
| 1,1-Dimethyl-6-tert-butyl-4-acetyl-indane | 0.5 |
| Coumarin | 3 |
| Trichloromethylphenylcarbinyl acetate | 1.5 |
| Tarragon, 10 %* | 3 |
| Oak moss absolute, 50 %* | 6 |
| Benjoin resinoid, 10 %* | 1.5 |
| Cinnamic alcohol of styrax | 1.5 |
| Jasmin absolute | 1.5 |
| Rose absolute | 1 |
| Cyclopentadecanolide, 10 %* | 2 |
| Methylnonylacetic aldehyde | 1.5 |
| Diethyl phthalate | 0.5 |
| Total | 100.0 |

*in ethyl phthalate

By adding to 99.0 g of this mixture 1.0 g of a (10) %* solution of 2,6,6-trimethyl-1-[1,3-dioxo-but-1-yl]-cyclohex-2-ene a more powerful composition than the basic composition is obtained. The new composition moreover possesses a more natural character that the basic composition and an olfactive note of a herb-like type reminiscent of aromatic plants such as marjoram.
* in ethyl phthalate By replacing in the present Example 2,6,6-trimethyl-1-[1,3-dioxo-but-1-yl]-cyclohex-2-ene by 2,6,6-trimethyl-1-[1,3-dioxo-but-1-yl]-cyclohex-1-ene, 2,6,6-trimethyl-1-[3-hydroxybutan-1-oyl]-cyclohex-2-ene or 2-methylene-6,6-dimethyl-1-[1,3-dioxo-but-1-yl]-cyclohexane, similar effects, although less pronounced, were observed. In particular, by using 2,6,6-trimethyl-1-[2-methyl-1,3-dioxo-but-1-yl]-cyclohex-2-ene in the proportions indicated above, a composition having a rather marked herb-like character was obtained. The fragrance of the new composition was reminiscent of the odour of certain tobaccos and moreover possessed an animal note of a slightly musk-like character.

EXAMPLE 4

Flavouring composition of the "Tutti-Frutti" type

A flavouring composition of the Tutti-Frutti type is prepared by mixing the following ingredients (parts by weight):

| | |
|---|---|
| Vanillin | 20 |
| Allyl caproate | 10 |
| Citral | 20 |
| Amyl butyrate | 35 |
| Orange oil | 45 |
| Ethyl butyrate | 75 |
| Ethyl acetate | 185 |
| Amyl acetate | 185 |
| Lemon oil | 415 |
| Total | 990 |

By the addition of 10 g of 2,6,6-trimethyl-1-[1,3-dioxo-but-1-yl]-cyclohex-2-ene to 990 g of the above mixture a "test" composition is obtained. The "check" composition is prepared by the addition of 10 g of lemon oil to the above mixture.

The foodstuffs described below are flavoured by using the proportions indicated (per 100 kg of foodstuff) by means of the test and check compositions:

| | |
|---|---|
| Cake | 20 g |
| Custard | 5 – 10 g |
| Candy | 15 – 20 g |

Candy: A mixture of 100 ml of sugar syrup (prepared by dissolving 1 kg of sucrose in 600 ml of water) and 20 g of glucose is slowly heated to 145°C. The flavour is added thereto, and it is allowed to harden while cooling.

Custard: A mixture of 60 g of sucrose and 3 g of pectin is added to 500 ml of warm milk, while stirring. The mixture is heated to the boil for a few seconds, the flavour is added, and the whole is allowed to cool.

Cake: The following ingredients are intimately mixed: 100 g of vegetable margarine, 1.5 g of NaCl, 100 g of sucrose, 2 eggs and 100 g of flour. The flavour is added, and the mass is cooked in the oven for 40 minutes at 180° C.

The finished foodstuffs are subjected to a panel of experts who have to express their opinions as to the value of the samples. All the members of the group were in agreement, when stating without any hesitation, that the taste of the test samples was more rounded-off than that of the check samples and that at the same time it had a floral, woody, camphor-like character. The camphor-like note is reminiscent of turpentine or the taste of certain berries such as bilberries.

By replacing in the above Example 2,6,6-trimethyl-1-[1,3-dioxo-but-1-yl]-cyclohex-2-ene by 2,6,6-trimethyl-1-[1,3-dioxo-but-1-yl]-cyclohex-1-ene the corresponding test samples have an analogous organoleptic note. Similar, but less pronounced effects, were obtained by the use of 2,6,6-trimethyl-1-[3-hydroxy-butan-1-oyl]-cyclohex-2-ene or 2,6,6-trimethyl-1-[3-hydroxy-butan-1-oyl]-cyclohex-1-ene.

The compounds of formula II used as starting materials in the process of this invention can be prepared according to the synthetic method described in U.S. copending application serial No. filed in the U.S. Patent Office on Mar. 21, 1973. The above application is entitled "New Nitrogen Derivatives, their Use and Process for Preparing same", the inventors are George Hermann Büchi and John Christopher Vederas. This copending application is assigned to the same assignee as this application.

For example, a compound of the formula II can be prepared by reacting a compound of formula

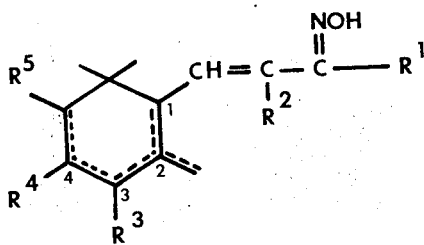

wherein the dotted lines as well as the symbols $R^1$, $R^2$, $R^3$, $R^4$ and $R^5$ have the same meaning as aforeindicated, with a halogen, e.g. iodine or bromine, or with a donor of positive halogen, e.g. N-bromosuccinimide to provide an isoxazole derivative of formula

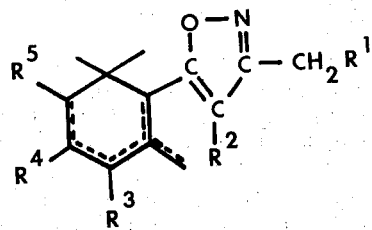

which upon catalytic hydrogenation yields the amino derivatives of formula II.

The nitrogen derivatives used as starting materials in the above mentioned process can be prepared by reacting $\alpha,\beta$-unsaturated ketones of formula

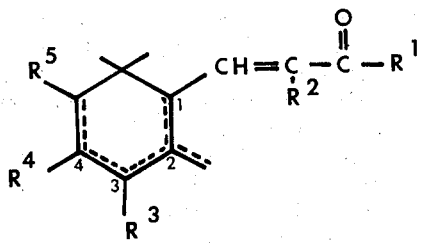

(wherein the substituents $R^1$, $R^2$, $R^3$, $R^4$ and $R^5$ and the dotted lines are defined as aforesaid) with hydroxylamine, generally in the form of its hydrochloride, according to the conventional techniques (cf. in this respect: L. F. Fieser and M. Fieser, Organic Chemistry, Reinhold Publ. Corp., New York (1956), p. 211 ff.)

The hereinabove indicated ketones represent a class of derivatives which are better known under the name of ionones and whose preparation has been thoroughly studied and described, viz. in Helv. Chim. Acta, 30, 2213 (1947); idem, 30, 2216 (1947); Fortschritte der Chemie organischer Naturstoffe, VIII, 146 (1951); J. Chem. Soc., 1074 (1951); J. Org. Chem., 32, 180 (1967). Some of the said compounds are commercially available.

The formation of the isoxazoles is preferably effected by means of iodine. This latter is maintained, at least partially, in solution in an aqueous medium by the addition of an alkali metal iodide, e.g. potassium iodide.

The cyclization reaction is preferably performed in an aqueous medium in the presence of an inert organic solvent such as an alcohol, e.g. methanol, ethanol, n-propanol or isopropanol, or in the presence of an ether, e.g. ethyl ether, dioxan, tetrahydroguran, monoglyme or diglyme. Methyl alcohol or tetrahydrofuran are preferred.

The said cyclization may occur in a wide temperature range. The formation of the desired isoxazole was observed at temperatures from 25° to 50°C. However, it is perferred to operate at temperatures higher than those aforeindicated. Indeed, it has been found that the best yields of final product were obtained when the cyclization was effected at the boiling temperature of the chosen solvent or at a temperature in the vicinity thereof. Of course, higher temperatures can also be used, in particular when the operation is carried out at a pressure exceeding the atmospheric pressure.

The reaction time can also vary within a wide range. Thus, if the reaction is carried out at a temperature from about 60° to about 80°C, good yields of final product are obtained within a reaction time comprised between about 1 hour and about 24 hours. Generally 2 1/2 hours are sufficient for the complete conversion of the compounds of formula

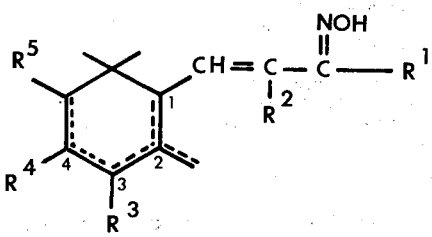

into their cyclic derivatives. As mentioned above, the reaction is preferably carried out in a neutral or alkaline medium. pH Values comprised between about 7 and about 12 can be conveniently used. In order to attain and to maintain in the course of the reaction this preferred acidity a buffer can be used, e.g. a boric or phosphoric salt of an alkali metal, e.g. sodium tetraborate, or sodium or potassium mono- or dihydrogenophosphate, or sodium hydrogenocarbonate. For reasons of economy the last mentioned buffer reagent is preferred.

When iodine is used as the cyclizing agent, the reaction is preferably carried out in the absence of light; however, this condition is not essential.

Working examples of how these compounds can be prepared are set forth in the specific examples given above.

I claim:

1. Process for the preparation of compounds of formula

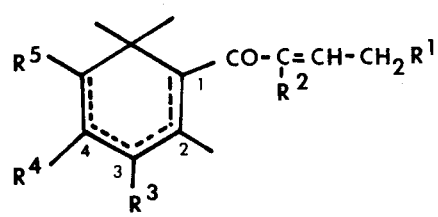

III possessing one cyclic double bond at position 1, 2, 3, or 4, or two conjugated double bonds at position 1 and 3 as indicated by the dotted lines and wherein the symbols $R^1$ and $R^2$ represent a hydrogen atom or one of them represents a lower alkyl group containing from 1 to 6 carbon atoms, and the symbols $R^3$, $R^4$ and $R^5$ all represent a hydrogen atom or one of them represents a lower alkyl group containing from 1 to 6 carbon atoms and the other ones represent a hydrogen atom, which comprises i. hydrolizing a compound of formula

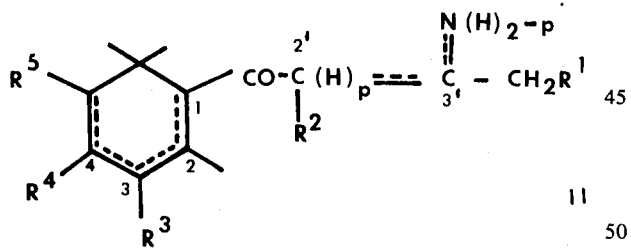

II wherein the index p stands for the integers zero or 1, the dotted lines and the symbols $R^1$ to $R^5$ possess the meaning aforeindicated and wherein the side chain has a double bond at position 2' ($p$ = zero) or 3' ($p$ = 1) in solution in an aqueous organic solvent at a temperature from about 15°C to about the boiling temperature of the chosen solvent and in the presence of an acidic agent to afford a compound of formula

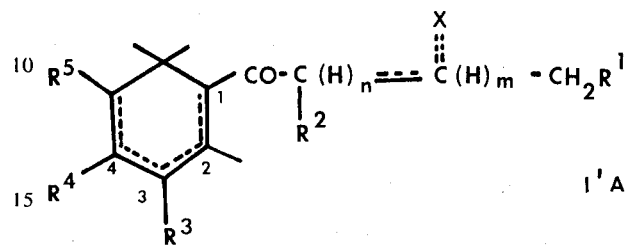

I'A wherein both indexes m and n stand for the integers zero or 1, the dotted lines and symbols $R^1$ and $R^5$ possess the meaning aforeindicated, the side chain can contain a double bond at position 2' or 3' and wherein the symbol X represents an oxygen atom ($m$ = zero; $n$ = 1) or a hydroxyl radical ($m$ and $n$ = zero);

ii. reducing the keto-derivative thus obtained by means of a catalytic hydrogenation to afford a compound of formula

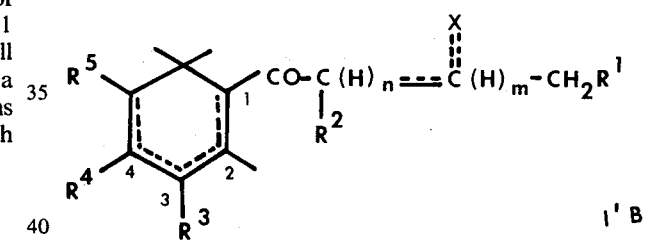

I'B wherein indexes m and n both stand for 1, the dotted lines and the symbols $R^1$ to $R^5$ possess the meaning aforeindicated and wherein the symbol X represents a hydroxyl radical; and finally iii. dehydrating the thus obtained hydroxy-derivative by means of an acidic or basic agent.

2. Process according to claim 1 wherein the acidic dehydration agent is a mineral or an organic acid.

3. Process according to claim 1 wherein the acidic dehydration agent is sulfuric, hydrochloric, boric, phosphoric or p-toluenesulfonic acid.

* * * * *

UNITED STATES PATENT AND TRADEMARK OFFICE
CERTIFICATE OF CORRECTION

PATENT NO. : 3,968,161
DATED : July 6, 1976
INVENTOR(S) : Karl-Heinrich Schulte-Elte It is certified that error appears in the above-identified patent and that said Letters Patent are hereby corrected as shown below:

Abstract, line 3 "flavoring" should be --flavouring--

Column 4, line 34 "or" should be --of--

Column 9, line 63 "77g..." should be --(a) 77g...--

Column 10, line 47 "3-methyl-3-" should be --3-methyl-5- --

Column 10, line 57 "4.10g" should be --(c) 4.10g--

Column 11, lines 44-45 "solution bicarbonate" should be
-- solution of sodium bicarbonate--

Column 14, line 69 "methylbut-" should be --methyl-but- --

Column 16, line 17 "butan-loyl" should be --butan-1-oyl--

Column 16, line 50 "$D^{20}$" should be --$d^{20}$ --

Column 17, line 1 "IR: 3400 cm $^1$" should be --IR: 3400 $cm^{-1}$--

Column 17, lines 3-4 "153 (11); 135 (11); 135 (7);"
should be --153 (11); 135 (7);--

Column 17, line 7 "-but-1-(-yl])"should be -- -but-1-yl]--

Column 17, line 57 "(10)%*" should be --10%*--

Column 17, line 68 "hydroxybutan" should be --hydroxy-butan--

UNITED STATES PATENT AND TRADEMARK OFFICE
CERTIFICATE OF CORRECTION

PATENT NO. : 3,968,161
DATED : July 6, 1976
INVENTOR(S) : Karl-Heinrich Schulte-Elte It is certified that error appears in the above-identified patent and that said Letters Patent are hereby corrected as shown below:

Column 18, line 35 "test and check" should be --"test" and "check"--

Column 18, lines 59 and 67 "test" should be --"test"

Column 18, line 60 "check" should be--"check"--

Column 19, lines 7-8 "...serial No. filed in the U.S. Patent Office on Mar. 21, 1973." should be -- ...serial No. 343,490, filed in the U.S. Patent Office Mar.21, 1973, now U.S. Patent No. 3,931,323.--

Signed and Sealed this

Sixteenth Day of November 1976

[SEAL]

Attest:

RUTH C. MASON
Attesting Officer

C. MARSHALL DANN
Commissioner of Patents and Trademarks